(12) United States Patent
Deshmukh

(10) Patent No.: US 12,138,400 B2
(45) Date of Patent: Nov. 12, 2024

(54) CATHETER SHAFT WITH UNIFORM BENDING STIFFNESS CIRCUMFERENTIALLY

(71) Applicant: MEDTRONIC CV LUXEMBOURG S.A.R.L., Luxembourg (LU)

(72) Inventor: Susheel Deshmukh, Santa Rosa, CA (US)

(73) Assignee: MEDTRONIC CV LUXEMNOURG S.A.R.L., Luxembourg (LU)

( * ) Notice: Subject to any disclaimer, the term of this patent is extended or adjusted under 35 U.S.C. 154(b) by 0 days.

(21) Appl. No.: 18/487,274

(22) Filed: Oct. 16, 2023

(65) Prior Publication Data

US 2024/0033474 A1 Feb. 1, 2024

Related U.S. Application Data

(62) Division of application No. 16/705,318, filed on Dec. 6, 2019, now Pat. No. 11,819,629.

(51) Int. Cl.
*A61M 25/00* (2006.01)
*A61F 2/24* (2006.01)
(Continued)

(52) U.S. Cl.
CPC ....... *A61M 25/0045* (2013.01); *A61F 2/2436* (2013.01); *A61F 2/966* (2013.01);
(Continued)

(58) Field of Classification Search
CPC .. A61F 2/95–97; A61F 2/2427–2/2439; B29C 48/001; B29C 48/0011;
(Continued)

(56) References Cited

U.S. PATENT DOCUMENTS 3,825,036 A 7/1974 Stent
5,222,949 A 6/1993 Kaldany
(Continued)

FOREIGN PATENT DOCUMENTS

CN 101166552 A 4/2008
WO 2006116719 A2 11/2006
WO 2006116720 A2 11/2006

OTHER PUBLICATIONS

Written Opinion and International Search Report issued Mar. 16, 2021 in International Appl. No. PCT/EP2020/084519.
(Continued)

*Primary Examiner* — Kathleen S Holwerda
(74) *Attorney, Agent, or Firm* — MEDLER FERRO WOODHOUSE & MILLS PLLC

(57) ABSTRACT

A catheter shaft includes an inner layer defining an innermost circumferential surface of the catheter shaft and defining a lumen of the catheter shaft, and an outer layer defining an outermost circumferential surface of the catheter shaft. The inner layer is formed by a first polymer having a first durometer and a first melting temperature. The outer layer is formed by alternating first and second segments of the first polymer and a second polymer, respectively, that alternate in a circumferential direction. The second polymer has a second durometer softer than the first durometer and a second melting temperature lower than the first melting temperature. Each segment of the alternating first and second segments extend in an axial direction for substantially an entire length of the catheter shaft. A method of forming the catheter shaft via extrusion is also disclosed.

20 Claims, 6 Drawing Sheets

(51) Int. Cl.
- *A61F 2/95* (2013.01)
- *A61F 2/966* (2013.01)
- *A61L 29/04* (2006.01)
- *A61M 25/16* (2006.01)
- *B29C 48/00* (2019.01)
- *B29C 48/09* (2019.01)
- *B29L 31/00* (2006.01)

(52) U.S. Cl.
CPC ....... *A61L 29/049* (2013.01); *A61M 25/0009* (2013.01); *B29C 48/0021* (2019.02); *B29C 48/09* (2019.02); *B29L 2031/7542* (2013.01)

(58) Field of Classification Search
CPC ............ B29C 48/0013; B29C 48/0015; B29C 48/0021; A61M 25/0045; A61M 25/005; A61M 25/0051; A61M 25/0053; A61M 25/0054; A61M 25/0009; A61M 25/001; A61M 25/0012; A61M 25/0013; A61M 25/1036

See application file for complete search history.

(56) References Cited

U.S. PATENT DOCUMENTS

| | | |
|---|---|---|
| 5,334,171 A | 8/1994 | Kaldany |
| 6,554,841 B1 | 4/2003 | Yang |
| 8,579,963 B2 | 11/2013 | Tabor |
| 9,757,536 B2 | 9/2017 | Abt et al. |
| 2006/0111771 A1 | 5/2006 | Ton et al. |
| 2008/0208128 A1 | 8/2008 | Guo et al. |
| 2009/0318863 A1 | 12/2009 | Chen |
| 2011/0172765 A1 | 7/2011 | Nguyen et al. |
| 2012/0035722 A1 | 2/2012 | Tuval |
| 2012/0101572 A1 | 4/2012 | Kovalsky et al. |
| 2013/0006174 A1 | 1/2013 | Phan |
| 2015/0273203 A1* | 10/2015 | Kitada ............... A61M 25/0009 264/173.17 |
| 2016/0158509 A1 | 6/2016 | Wedan et al. |
| 2017/0056171 A1 | 3/2017 | Cooper et al. |
| 2019/0134348 A1 | 5/2019 | Wada |

OTHER PUBLICATIONS

Notice of Rejection dated Jul. 2, 2024 in CN Appl. No. 202080083320.1.

* cited by examiner

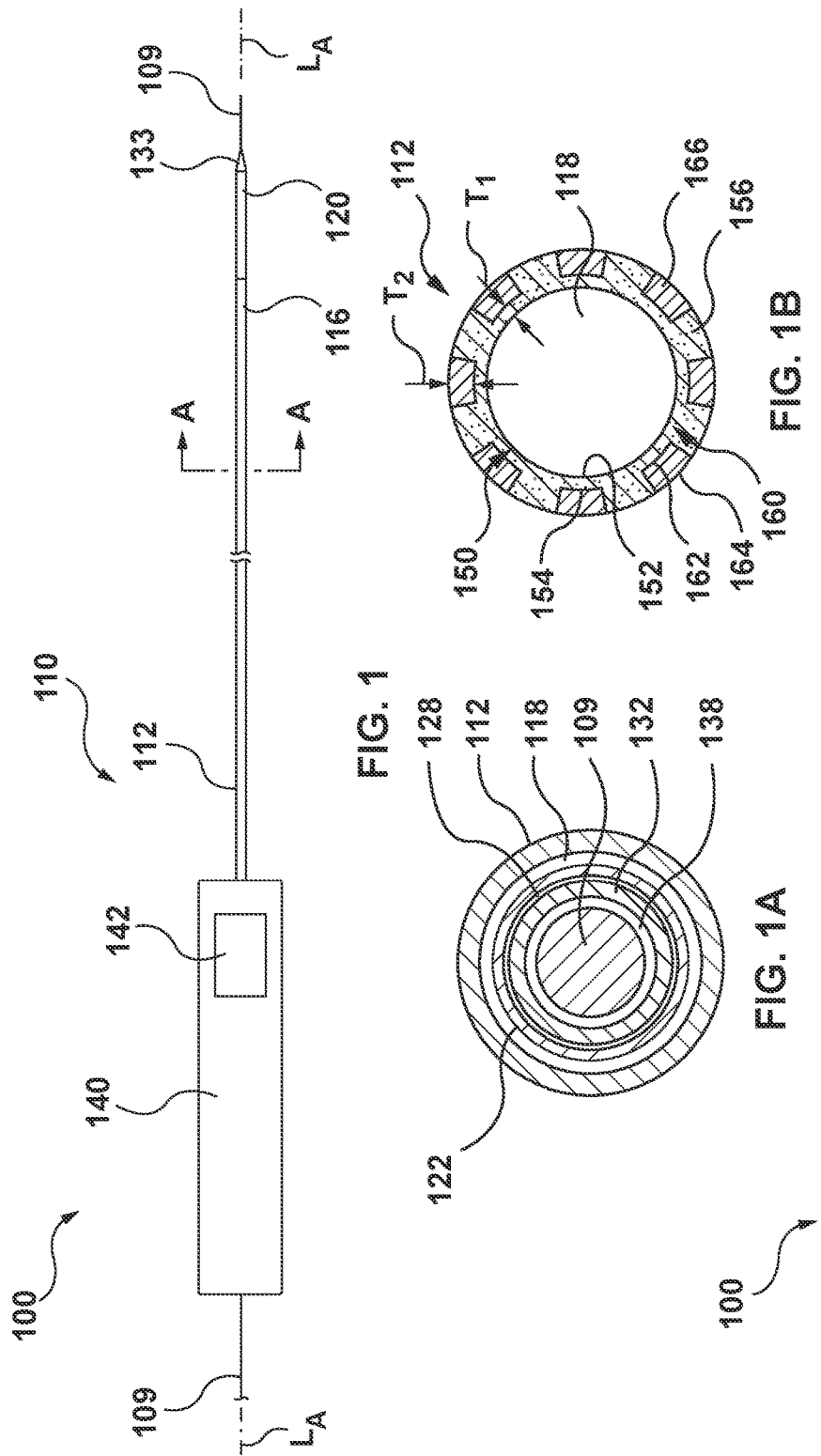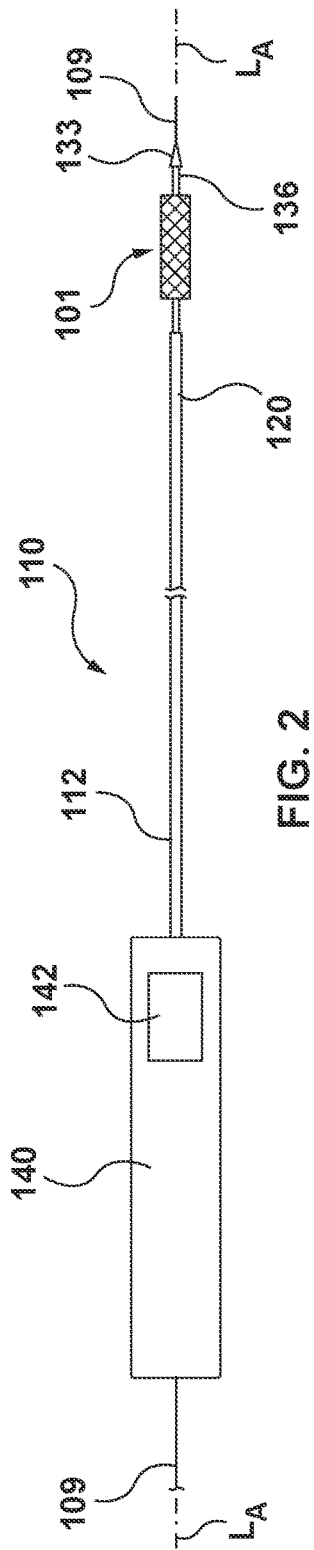

CATHETER SHAFT WITH UNIFORM BENDING STIFFNESS CIRCUMFERENTIALLY

CROSS-REFERENCE TO RELATED APPLICATIONS

This application is a divisional of U.S. patent application Ser. No. 16/705,318, filed Sep. 22, 2017, now allowed, which is incorporated by reference herein in its entirety.

FIELD OF THE INVENTION

The present invention is related to catheters, and is more particularly related to the construction of a catheter shaft.

BACKGROUND

Among devices commonly used to access vascular and other locations within a body and to perform various functions at those locations are medical catheters, or delivery catheters, adapted to deliver and deploy medical devices such as prosthetic heart valves, stent-grafts, and stents to selected targeted sites in the body. Such medical devices typically are releasably carried within a distal region of the delivery catheter in a radially compressed delivery state or configuration as the catheter is navigated to and positioned at a target treatment/deployment site. In many cases, such as those involving cardiovascular vessels, the route to the treatment/deployment site may be tortuous and may present conflicting design considerations requiring compromises between dimensions, flexibilities, material selection, operational controls and the like.

Typically, advancement of a delivery catheter within a patient is monitored fluoroscopically to enable a clinician to manipulate the catheter to steer and guide its distal end through the patient's vasculature to the target treatment/deployment site. This tracking requires a distal end of the delivery catheter to be able to navigate safely to the target treatment/deployment site through manipulation of a proximal end by the clinician. Such manipulation may encompass pushing, retraction and torque forces or a combination of all three. It is therefore required for the distal end of the delivery catheter to be able to withstand all these forces.

A delivery catheter desirably will have a low profile/small outer diameter to facilitate navigation through tortuous vasculature; however, small outer diameter catheters present various design difficulties resulting from competing considerations, resulting in design trade-offs. For instance, such delivery catheters must be flexible enough to navigate the tortuous vasculature or anatomy of a patient. However, typical constructions of delivery catheters must attempt to balance a requisite flexibility, with axial strength/stiffness (the property that permits the delivery catheter to be pushed and pulled) and torsional strength/stiffness (the property that permits the delivery catheter to be rotated about its longitudinal axis). It is especially important to balance these properties in a distal portion of the delivery catheter within which a prosthesis is held in its radially compressed, delivery state.

A need in the art still generally exists for improved catheters configured to navigate through or within a patient's anatomy.

SUMMARY

Embodiments of the present invention relate generally a catheter shaft including an inner layer defining an innermost circumferential surface of the catheter shaft and defining a lumen of the catheter shaft, and an outer layer defining an outermost circumferential surface of the catheter shaft. The inner layer is formed by a first polymer having a first durometer and a first melting temperature. The outer layer is formed by alternating first and second segments of the first polymer and a second polymer, respectively, that alternate in a circumferential direction. The second polymer has a second durometer softer than the first durometer and a second melting temperature lower than the first melting temperature. Each segment of the alternating first and second segments extend in an axial direction for substantially an entire length of the catheter shaft.

Embodiments hereof also relate to a system including a self-expanding prosthesis and a delivery device configured to percutaneously deliver the self-expanding prosthesis. The delivery device includes a handle having an actuator thereon, an outer sheath including a proximal end coupled to the handle, a middle shaft slidingly disposed within the outer sheath, the middle shaft having a proximal end coupled to the handle and a distal end configured to releasably couple to the self-expanding prosthesis such that the self-expanding prosthesis axially moves therewith when coupled to thereto, an inner shaft disposed within the middle shaft, wherein the self-expanding prosthesis is disposed on a distal portion of the inner shaft during delivery thereof. At least one of the outer sheath and the middle shaft include an inner layer defining an innermost circumferential surface and an outer layer defining an outermost circumferential surface. The inner layer is formed by a first polymer having a first durometer and a first melting temperature. The outer layer is formed by alternating first and second segments of the first polymer and a second polymer, respectively, that alternate in a circumferential direction. The second polymer has a second durometer softer than the first durometer and a second melting temperature lower than the first melting temperature. Each segment of the alternating first and second segments extend in an axial direction for substantially an entire length of the at least one of the outer sheath and the middle shaft.

Embodiments hereof also relate to a method of forming a catheter shaft. A first component is extruded, the first component being formed of a first polymer having a first durometer and a first melting temperature. The first component includes an inner layer defining an innermost circumferential surface and a plurality of segments radially extending from the inner layer. A notch extends between each pair of adjacent segments of the plurality of segments. Each segment of the plurality of segments extends in an axial direction for substantially an entire length of the inner layer. An elongated tube of a second polymer having a second durometer and a second melting temperature is positioned into each notch. The second durometer is softer than the first durometer and the second melting temperature is lower than the first melting temperature. The elongated tubes of the second polymer are heated to fuse the elongated tubes of the second polymer to the first component and thereby form the catheter shaft. The catheter shaft has a smooth and continuous outermost circumferential surface after the step of heating the elongated tubes of the second polymer.

BRIEF DESCRIPTION OF THE DRAWINGS

The accompanying figures, which are incorporated herein, form part of the specification and illustrate embodiments of a delivery system. Together with the description, the figures further explain the principles of and enable a FIG. 1 is a side view of a delivery system according to an embodiment hereof.

FIG. 1A is a cross-sectional view of the delivery system of FIG. 1 taken along line A-A of FIG. 1.

FIG. 1B is an enlarged cross-sectional view of the outer sheath of the delivery system of FIG. 1, wherein the outer sheath is removed from the delivery system for illustrative purposes only.

FIG. 2 is a side view of the delivery system of FIG. 1, wherein the delivery system is in a deployed configuration.

DETAILED DESCRIPTION OF THE INVENTION

Figure 1C:
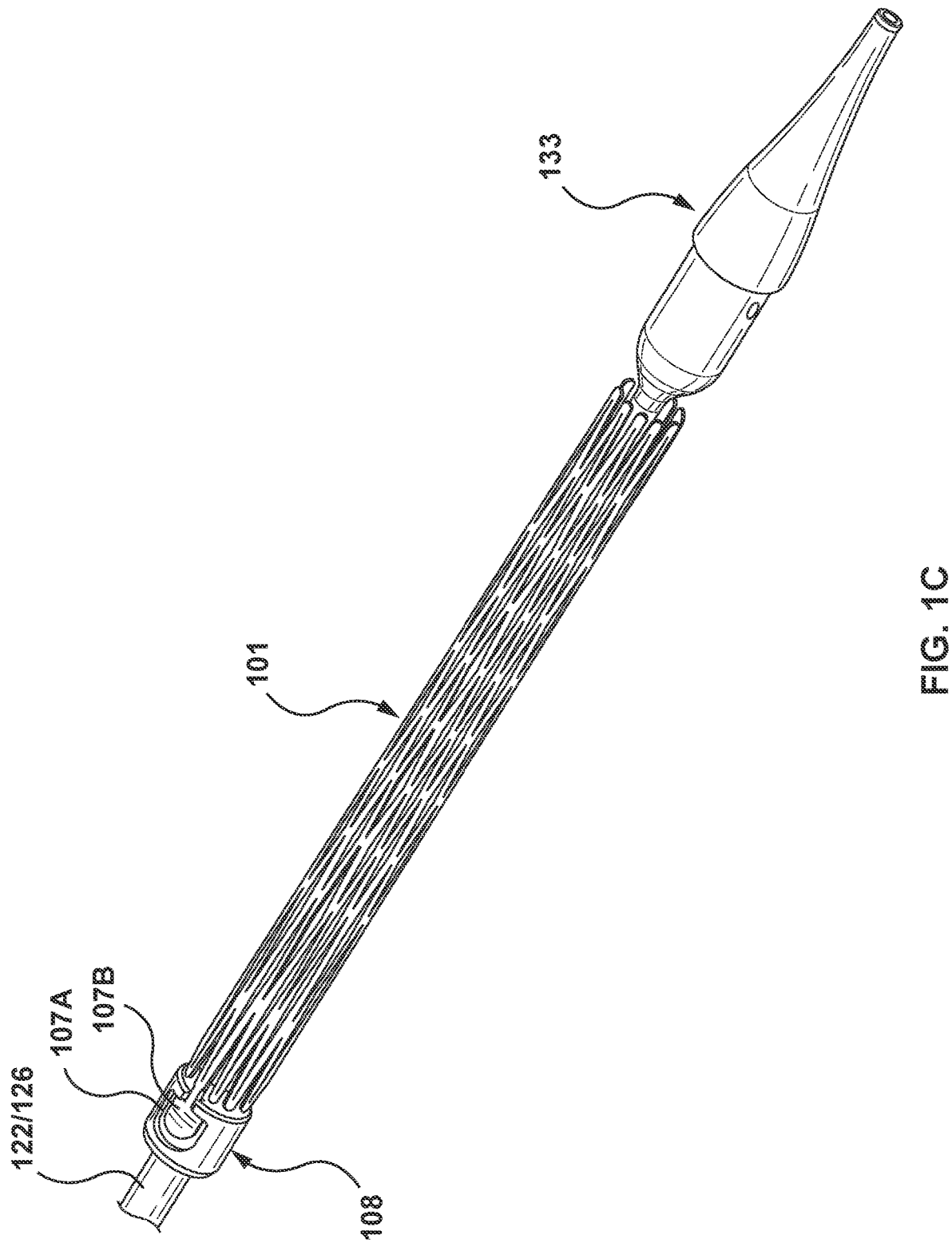
FIG. 1C is a perspective view of a distal portion of the delivery system of FIG. 1, wherein the delivery system is in the delivery configuration and an outer sheath of the delivery system is not shown for illustrative purposes only.

Specific embodiments of the present invention are now described with reference to the figures, wherein like reference numbers indicate identical or functionally similar elements. Unless otherwise indicated, the terms "distal" and "proximal", when used in the following description to refer to a sheath, a delivery device, or a catheter-based delivery system are with respect to a position or direction relative to the treating clinician. Thus, "distal" and "distally" refer to positions distant from, or in a direction away from the treating clinician, and the terms "proximal" and "proximally" refer to positions near, or in a direction toward the treating clinician. The terms "distal" and "proximal", when used in the following description to refer to a device to be implanted into a vessel, such as a heart valve prosthesis, are used with reference to the direction of blood flow. Thus, "distal" and "distally" refer to positions in a downstream direction with respect to the direction of blood flow, and the terms "proximal" and "proximally" refer to positions in an upstream direction with respect to the direction of blood flow.

In addition, the term "self-expanding" is used in the following description with reference to one or more stent structures of the prostheses hereof and is intended to convey that the structures are shaped or formed from a material that can be provided with a mechanical memory to return the structure from a radially compressed or constricted delivery configuration to a radially expanded deployed configuration. Non-exhaustive illustrative self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

Embodiments hereof relate to catheter devices or delivery systems including at least one catheter shaft that includes an inner layer defining an innermost circumferential surface and an outer layer defining an outermost circumferential surface. The inner layer is formed entirely of a first polymer having a first durometer and a first melting temperature. The outer layer is formed by alternating segments of the first polymer and a second polymer that alternate in a circumferential direction. The second polymer has a second durometer that is softer than the first durometer and a second melting temperature that is lower than the first melting temperature. As described in more detail herein, such a catheter shaft has uniform bending stiffness in a circumferential direction. As used herein, bending stiffness refers to the resistance of the catheter shaft against bending deformation and a catheter shaft constructed according to embodiments hereof has uniform or unvarying bending stiffness in all circumferential directions. The following detailed description is merely exemplary in nature and is not intended to limit the invention or the application and uses of the invention. Furthermore, there is no intention to be bound by any expressed or implied theory presented in the preceding technical field, background, brief summary, or the following detailed description. Although the description of the invention is primarily in the context of a prosthetic valve delivery system, the catheter shaft construction described herein may be utilized in any type of catheter device or delivery system.

A delivery system including at least one catheter shaft having uniform bending stiffness in a circumferential direction will be described in more detail with reference to the figures. A delivery system 100 includes a self-expanding prosthesis 101 and a delivery device 110 configured to percutaneously deliver the self-expanding prosthesis 101. More particularly, the delivery system 100 is shown in FIGS. 1, 1A, 1B, 1C, and 2. FIG. 1 is a side view of the delivery system 100, with an outer sheath 112 thereof shown in a delivery configuration in which the outer sheath 112 surrounds and constrains the self-expanding prosthesis 101 (not shown in FIG. 1A) in a compressed or delivery configuration. FIG. 1A is a cross-sectional view taken along line A-A of FIG. 1A. FIG. 1B is an enlarged cross-sectional view of the outer sheath 112 removed from the delivery system 100 for illustrative purposes only. FIG. 1C is a perspective view of a distal portion of the delivery system 100 in the delivery configuration but with the outer sheath 112 not shown for illustrative purposes only. FIG. 2 is a side view of the delivery system 100 after the outer sheath 112 has been retracted to allow the prosthesis 101 to self-expand to a deployed or expanded configuration. The delivery device 110 includes a handle 140 having an actuator 142 thereon. The handle 140 can have any shape or size appropriate for convenient handling by a user.

In addition to the outer sheath 112 operatively coupled to the handle 140, the delivery device 110 further includes a middle shaft 122 slidingly disposed within the outer sheath 112 and operatively coupled to the handle 140, and an inner shaft 132 disposed within the middle shaft 122. As used herein, "slidably" denotes back and forth movement in a longitudinal direction along or generally parallel to a central longitudinal axis LA of the delivery system 100. The outer sheath 112, the middle shaft 122, and the inner shaft 132 each distally extend from within the handle 140.

The outer sheath 112 has a proximal end disposed within the handle 140 and a distal end 116. As best shown in FIG. 1A, the outer sheath 112 defines a lumen 118 and is slidingly and concentrically disposed over the middle shaft 122. A distal portion of the outer sheath 112 defines a capsule 120. The capsule 120 is configured to retain the self-expanding prosthesis 101 in a radially collapsed configuration for delivery to the desired treatment location as will be described in more detail herein. While the capsule 120 is described herein as a distal portion of the outer sheath 112, the capsule 120 may be a separate component coupled to the distal end of the outer sheath 112. If formed as a separate component, the capsule 120 may include a relatively short, tapered proximal end that is attached to a distal end of the outer shaft 112 by any suitable attachment means. When the capsule 120 is a separate component than the outer shaft 112, the capsule 120 may be formed with the same constructions as outer shaft 112 such that the capsule 120 also has uniform bending stiffness in a circumferential direction. If formed as a separate component, the capsule 120 may be larger in both inner diameter and outer diameter than the outer shaft 112. For example, the capsule 120 may be formed with an inner diameter of ranging between 0.195 and 0.215 inches and an outer diameter of ranging between 0.215 and 0.235 inches. Conversely, the outer shaft 112 may be formed with an inner diameter of approximately 0.120 inches and an outer diameter of approximately 0.160 inches. The middle shaft 122 may be formed with an inner diameter of approximately 0.050 inches and an outer diameter of approximately 0.110 inches.

The actuator 142 of the handle 140 is configured for retracting the capsule 120. The actuator 142 is coupled to the outer sheath 112, and is generally constructed to provide selective proximal retraction and distal advancement of the outer sheath 112, and particularly of the capsule 120 attached thereto, relative to the self-expanding prosthesis 101 held in a radially compressed, delivery configuration therein for covering and uncovering the self-expanding prosthesis 101. The actuator 142 may assume any construction that is capable of providing the desired sheath actuation functionality, such as those described in U.S. Pat. No. 8,579,963 to Tabor, which is assigned to the same assignee as the present disclosure and which is herein incorporated by reference in its entirety.

The middle shaft 122 has a proximal end disposed within the handle 140 and a distal end 126 disposed inside of the outer sheath 112 when the outer sheath 112 is disposed over the self-expanding prosthesis 101. The distal end 126 of the middle shaft 122 includes a spindle 108 which is releasably coupled to an end of the self-expanding prosthesis 101. As best shown on the perspective view of FIG. 1C, having the outer sheath 112 removed for illustrative purposes only, the spindle 108 is a tubular component having at least one recess 107A formed on an outer surface thereof that is configured to receive a paddle 107B extending proximally from the self-expanding prosthesis 101. The paddle 107B fits within or mates with the recess 107A of the spindle 108 such that the self-expanding prosthesis 101 is releasably coupled to middle shaft 122. Although only one recess 107A is visible on FIG. 1B, it will be understood by one of ordinary skill in the art that the spindle 108 may include two or more recesses for receiving a mating paddle of the self-expanding prosthesis 101, such as for example first and second recesses at opposing circumferential locations on the spindle 108. As best shown in FIG. 1A, the middle shaft 122 defines a lumen 128 and is concentrically disposed over the inner shaft 132. The inner shaft 132 has a proximal end (not shown) which terminates within the handle 140 and a distal end 136. A tapered flexible nosecone or distal tip 133 may be coupled to the distal end 136 of the inner shaft 132 as shown in FIG. 1 and FIG. 2. As best shown in FIG. 1A, the inner shaft 132 defines a lumen 138 such that the delivery system 100 may be slidingly disposed and tracked over a guidewire 109. The inner shaft 132 is coupled to the middle shaft 122 at the spindle 108 such that the inner shaft 132 and the middle shaft 122 are slidingly disposed within the outer sheath 112 as an assembly.

The inner shaft 132 is configured to receive the self-expanding prosthesis 101 on a distal portion thereof and the outer sheath 112 is configured to compressively retain the self-expanding prosthesis 101 on the distal portion of the inner shaft 132 during delivery, as shown in FIG. 1. Stated another way, the outer sheath 112 surrounds and constrains the self-expanding prosthesis 101 in a radially compressed or delivery configuration. As previously described, the distal end 126 of the middle shaft 122 includes the spindle 108 to which the self-expanding prosthesis 101 is releasably coupled. The self-expanding prosthesis 101 is shown in the view of FIG. 2 but is obscured from view by the outer sheath 112 in FIG. 1. During deployment of the self-expanding prosthesis 101 in situ, the outer sheath 112 is proximally retracted with respect to the self-expanding prostheses 101 via the actuator 142 on the handle 140, thereby incrementally exposing the self-expanding prosthesis 101 until the self-expanding prothesis 101 is fully exposed and thereby released from the delivery device 110. The middle shaft 122, the inner shaft 132 and the self-expanding prosthesis 101 are held stationary while the outer sheath 112 is proximally retracted. When the outer sheath 112 is proximally retracted beyond the spindle 108, the paddles 107B of the self-expanding prosthesis 101 are no longer held within the recesses 107A of the spindle 108 and the self-expanding prosthesis 101 is permitted to self-expand to its deployed configuration.

Figure 3:
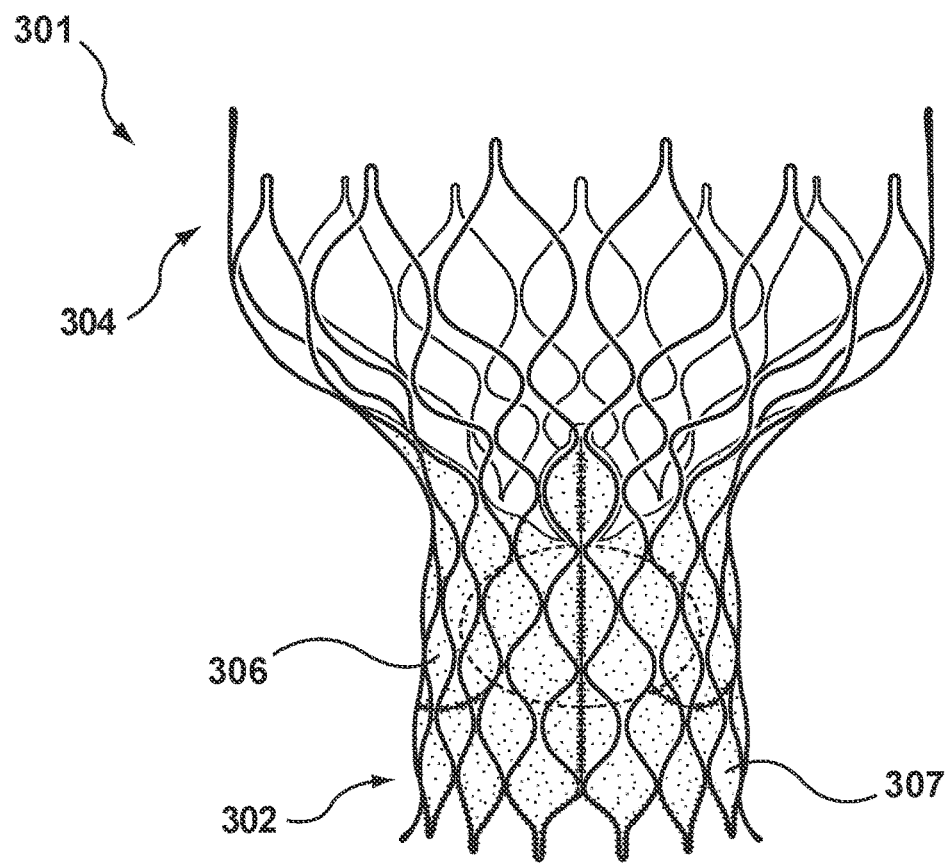
FIG. 3 is a side perspective view of a heart valve prostheses for use in embodiments hereof.
Figure 4:
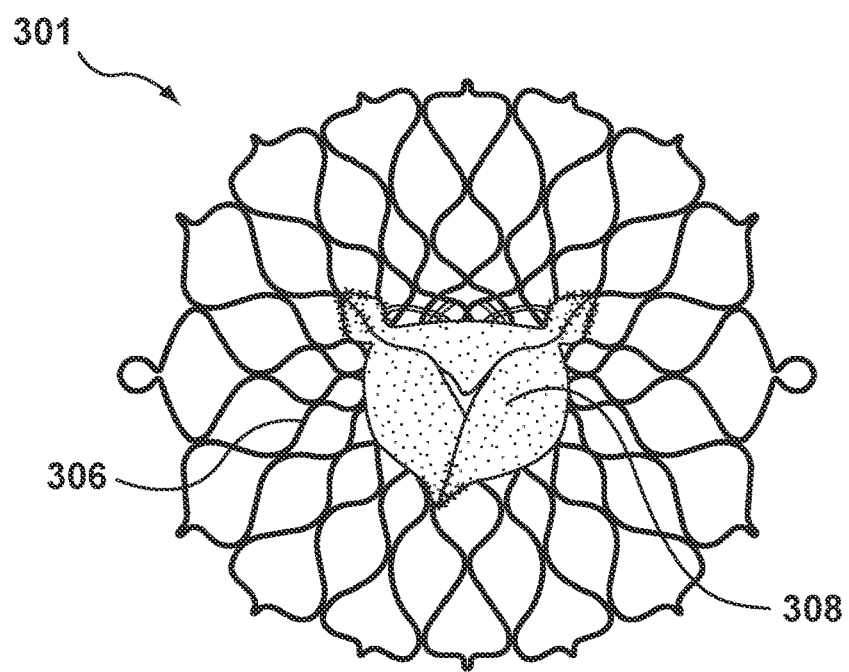
FIG. 4 is an end view of the heart valve prosthesis of FIG. 3.

FIG. 3 and FIG. 4 illustrate side perspective and end views, respectively, of a heart valve prosthesis 301 that may be utilized as the self-expanding prosthesis 101 according to an embodiment hereof. The heart valve prosthesis 301 is merely exemplary and is described in more detail in U.S. Patent Application Pub. No. 2011/0172765 to Nguyen et al., which is herein incorporated by reference in its entirety. It is understood that any number of alternate heart valve prostheses can be used with the delivery devices and methods described herein. In addition, the delivery device 110 may also be used with other self-expanding prostheses such as stent-graft prostheses, uncovered stents, bare metal stents, drug eluting stents, and any self-expanding structure.

Heart valve prosthesis 301 includes an expandable stent or frame 306 that supports a prosthetic valve component 308 within the interior of the frame 306. In embodiments hereof, the frame 306 is self-expanding to return to a radially expanded configuration from a radially compressed or constricted delivery configuration. In the embodiment depicted in FIGS. 3 and 4, the frame 306 has an expanded, longitudinally asymmetric hourglass configuration including a first end or portion 302 and a relatively enlarged second end or portion 304. Each portion of frame 306 may be designed with a number of different configurations and sizes to meet the different requirements of the location in which it may be implanted. When configured as a replacement for an aortic valve, the first end 302 functions as an inflow end of the heart valve prosthesis 301 and extends into and anchors within the aortic annulus of a patient's left ventricle, while the enlarged second end 304 functions as an outflow end of the heart valve prosthesis 301 and is positioned in the patient's ascending aorta. When configured as a replacement for a mitral valve, the enlarged second end 304 functions as an inflow end of the heart valve prosthesis 301 and is positioned in the patient's left atrium, while the first end 302 functions as an outflow end of the heart valve prosthesis 301 and extends into and anchors within the mitral annulus of a patient's left ventricle. For example, U.S. Patent Application Publication Nos. 2012/0101572 to Kovalsky et al. and 2012/0035722 to Tuval, each of which are herein incorporated by reference in their entirety, illustrate heart valve prostheses configured for placement in a mitral valve. Each portion of the frame 306 may have the same or different cross-portion which may be for example circular, ellipsoidal, rectangular, hexagonal, rectangular, square, or other polygonal shape, although at present it is believed that circular or ellipsoidal may be preferable when the valve prosthesis is being provided for replacement of the aortic or mitral valve. As alternatives to the deployed asymmetric hourglass configuration of FIGS. 3 and 4, the frame 306 may have a symmetric hourglass configuration, a generally tubular configuration, or other stent configuration or shape known in the art for valve replacement.

As previously mentioned, the heart valve prosthesis 301 includes the prosthetic valve component 308 within the interior of frame 306. The prosthetic valve component 308 is capable of blocking flow in one direction to regulate flow there through via valve leaflets that may form a bicuspid or tricuspid replacement valve. FIG. 4 is an end view of the heart valve prostheses 201 of FIG. 3 and illustrates an exemplary tricuspid valve having three leaflets, although a bicuspid leaflet configuration may alternatively be used in embodiments hereof. Valve leaflets are sutured or otherwise securely and sealingly attached to the interior surface of the frame 306 and/or graft material 307 which encloses or lines the frame 306 as would be known to one of ordinary skill in the art of prosthetic tissue valve construction. Leaflets may be attached along their bases to the graft material 307, for example, using sutures or a suitable biocompatible adhesive. Adjoining pairs of leaflets are attached to one another at their lateral ends to form commissures. The orientation of the leaflets within the frame 306 would change depending on which end of the heart valve prosthesis 301 is the inflow end and which end of the heart valve prosthesis 301 is the outflow end, thereby ensuring one-way flow of blood through the heart valve prosthesis 301.

Leaflets may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets include DACRON® polyester commercially available from Invista North America S.A.R.L. of Wilmington, DE, other cloth materials, nylon blends, polymeric materials, and vacuum deposition nitinol fabricated materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

The graft material 307 may also be a natural or biological material such as pericardium or another membranous tissue such as intestinal submucosa. Alternatively, the graft material 307 may be a low-porosity woven fabric, such as polyester, Dacron fabric, or PTFE, which creates a one-way fluid passage when attached to the stent. In one embodiment, the graft material 307 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

At least one of the middle shaft 122 and the outer sheath 112 is formed without or devoid of axial wires or other reinforcement structures and is constructed to have uniform bending stiffness in a circumferential direction. Since the inner shaft 132 is coupled to the middle shaft 122 at the spindle 108 such that the inner shaft 132 and the middle shaft 122 are slidingly disposed within the outer sheath 112 as an assembly as described above, it is not necessary for the inner shaft 132 to have uniform bending stiffness in a circumferential direction. However, if the inner shaft 132 is not attached to the middle shaft 122, it also may be constructed to have uniform bending stiffness in a circumferential direction as described herein. More particularly, catheter shafts that undergo very high tensile and compressive forces during operation (i.e., during deployment of a self-expanding prosthesis or during re-sheathing of a self-expanding prosthesis) are often longitudinally or axially reinforced with one or more axial wires that are disposed at circumferentially opposite locations. As used herein, very high tensile forces include forces between 10 lbf and 50 lbf and very high compressive forces include forces between 10 lbf and 50 lbf. However, catheter shafts constructed with such axial wires cannot bend in certain circumferential directions, which can contribute to tracking difficulty thereof in tortuous vasculature or anatomies such as an aortic arch. Catheter shafts constructed as described herein have uniform bending stiffness in a circumferential direction combined with ability to withstand very high tensile and compressive forces during operation due to the properties of two different polymer materials and the configuration of the inner and outer layers thereof. In the embodiment of FIGS. 1, 1A, 1B, 1C, and 2, both the middle shaft 122 and the outer sheath 112 are formed to have uniform bending stiffness in a circumferential direction as described herein. The construction of the outer sheath 112 is described in detail with respect to FIG. 1B. In an embodiment, the middle shaft 122 has the same layered construction as the outer sheath 112 as described with reference to FIG. 1B such that both the outer sheath 112 and the middle shaft 122 have the construction described. In another embodiment, only the middle shaft 122 is formed to have uniform bending stiffness in a circumferential direction and is formed with the layered construction described with reference to FIG. 1B. In another embodiment, only the outer sheath 112 is formed to have uniform bending stiffness in a circumferential direction and is formed with the layered construction described with reference to FIG. 1B.

As shown in FIG. 1B, which is an enlarged cross-sectional view of the outer sheath 112 removed from the delivery system 100 for illustrative purposes only, the outer sheath 112 includes a first or inner layer 150 that defines, forms, or otherwise includes an innermost circumferential surface 152 of the outer sheath 112 and a second or outer layer 160 that defines, forms, or otherwise includes an outermost circumferential surface 164 of the outer sheath 112. The inner layer 150 and the outer layer 160 directly contact each other with the outer layer 160 circumferentially surrounding the inner layer 150. More particularly, the inner layer 150 includes the innermost circumferential surface 152 and an outermost circumferential surface 154. In an embodiment, the innermost circumferential surface 152 may be textured to reduce friction. The inner layer 150 has a consistent thickness $T_1$ around the circumference thereof. The outer layer 160 includes an innermost circumferential surface 162 and the outermost circumferential surface 164. The outer layer 160 has a consistent thickness $T_2$ around the circumference thereof. The innermost circumferential surface 162 of the outer layer 160 contacts or abuts against the outermost circumferential surface 154 of the inner layer 150. In an embodiment, the inner layer 150 is thinner than the outer layer 160. For example, in an embodiment, the thickness $T_2$ of the outer layer 160 is between 2 and 10 times the thickness $T_1$ of the inner layer 150. In another embodiment, the thickness $T_2$ of the outer layer 160 is between 6 and 8 times the thickness $T_1$ of the inner layer 150. Exemplary relative pairings of thickness values, in inches, for thickness $T_1$ and thickness $T_2$ are shown in the table below.

| Thickness $T_1$ | 0.002" | 0.005" | 0.005" | 0.010" |
| Thickness $T_2$ | 0.018" | 0.015" | 0.025" | 0.020" |

The inner layer 150 is formed entirely or solely of a first polymer having a first durometer and a first melting temperature. The first polymer is a relatively hard polymeric material that has the ability to withstand very high tensile and compressive forces during operation such as but not limited to polyetheretherketone (PEEK). Other suitable polymers for the first polymer include PPS (Polyphenylene Sulfide), PPSU (Polyphenyl Sulfone), PEI (Polyetherimide), PET (Polyethylene Terephthalate), PBT (Polybuthylene Terephthalate), and PCT (Polycyclohexylenedimethylene Terephthalate). In an embodiment hereof, at body temperature, the first polymer has a tensile strength between 9,000 and 11,000 psi, a flexural strength between 19,000 and 21,000 psi, and a compressive strength between 14,000 and 16,000 psi. In another embodiment hereof, at body temperature, the first polymer has a tensile strength of 10,000 psi, a flexural strength of 20,000 psi, and a compressive strength of 15,000 psi.

The outer layer 160 is formed by alternating first and second segments 156, 166 of the first polymer and a second polymer, respectively, that alternate in a circumferential direction around the circumference of the outer layer 160. The segments of the first polymer are referred to herein as first segments 156 and the segments of the second polymer are referred to herein as second segments 166. As will be described herein in more detail with respect to FIGS. 5-8, in an embodiment, the inner layer 150 and the first segments 156 of the outer layer 160 are formed in a single piece construction by extrusion. The first segments 156 alternate with the second segments 166, or stated another way, each first segment 156 is disposed between a pair of the second segments 166 and each second segment 166 is disposed between a pair of the first segments 156. The second polymer has a second durometer softer than the first durometer of the first polymer. Further, the second polymer has a second melting temperature lower than the first melting temperature of the first polymer. The second polymer is a relatively soft polymeric material such as but not limited to thermoplastic polyurethane 80A that imparts flexibility to the outer sheath 112 and improves trackability of the delivery system 100. Other suitable polymers for the second polymer include thermoplastic polyether urethane (ELASTHANE, TECOTHANE, TECOFLEX, TEXIN), thermoplastic polycarbonate urethane (BIONATE), thermoplastic silicone urethane (PURSIL), C-FLEX, CHRONOPRENE, AND POLYBLEND. In an embodiment hereof, at body temperature, the second polymer has a flexural strength between 4,000 and 6,000 psi. In another embodiment hereof, at body temperature, the second polymer has a flexural strength of 5,000 psi.

Although only a cross-sectional view is shown in FIG. 1B, each segment of the alternating first and second segments 156, 166 extends in an axial direction for an entire length or substantially the entire length of the outer sheath 112. Stated another way, the cross-section of the outer sheath 112 is the same as shown in FIG. 1B along an entire length of the outer sheath 112. As used herein, "substantially the entire length" includes at least 95% of the total or entire length of the catheter shaft. The first segments 156 of the first polymer are circumferentially spaced apart at equal intervals around the circumference of the outer layer 160, and the second segments 166 of the second polymer are circumferentially spaced apart at equal intervals around the circumference of the outer layer 160. Each of the first segments 156 have the same size or width, and each of the second segments 166 have the same size or width, with the first segments 156 being equally circumferentially spaced apart from each other. In an embodiment, each segment of the alternating first and second segments 156, 166 are the same size or width although this is not required. Although FIG. 1B illustrates the outer layer 160 with eight first segments 156 and eight second segments 166, the total number of alternating first and second segments 156, 166 may vary. In an embodiment, the alternating first and second segments 156, 166 include at least five first segments 156 and at least five second segments 166. In an embodiment, the alternating first and second segments 156, 166 include between five and ten first segments 156 and between five and ten second segments 166.

The manufacturing of the catheter shafts having the layered construction described with reference to FIG. 1B is simplified as compared to catheter shafts including axial wires or other reinforcement structures. More particularly, manufacture of catheter shafts that include axial wires or other reinforcement structures require multiple processes across manufacturing sites such as extrusion, braiding, and fusing processes. Further, catheter shafts that include axial wires or other reinforcement structures often include a high number (i.e., 10 or more) components per shaft and must be manufactured one at a time due to the design thereof, thereby resulting in a relatively expensive cost of manufacture per shaft. In contrast, catheter shafts having the layered construction described with reference to FIG. 1B may be made using only three components (i.e., a core mandrel, the first polymer, and the second polymer). Further, catheter shafts having the layered construction described with reference to FIG. 1B may be made using a continuous extrusion process and multiple catheter shafts may be formed during the extrusion process in a batch-style method of manufacture, thereby resulting in a relatively less expensive cost of manufacture per shaft.

Figure 5:
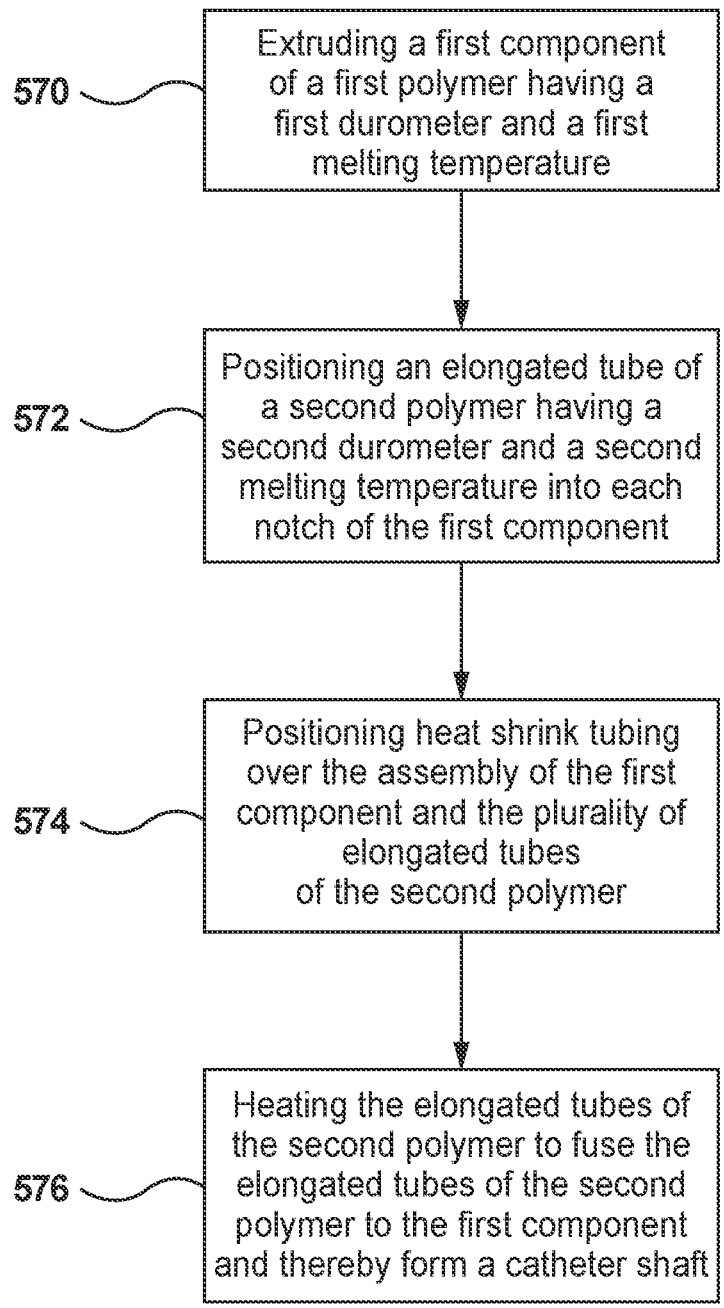
FIG. 5 is a flow chart illustrating a method of forming a catheter shaft to have uniform bending stiffness in a circumferential direction according to an embodiment hereof.
Figure 6:
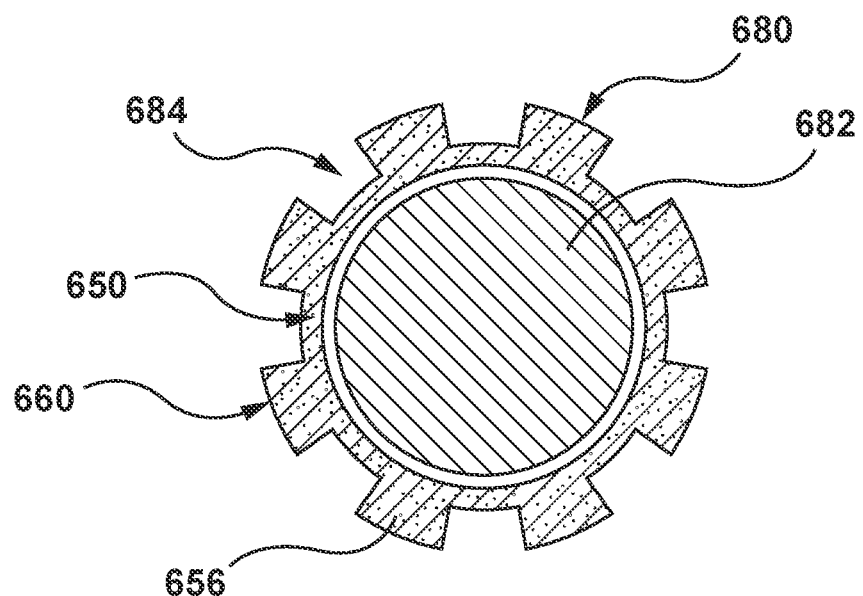
FIG. 6 is a cross-sectional view illustrating a first component of a first polymer described in the method of forming a catheter shaft of FIG. 5.

FIG. 5 is a flow chart illustrating a method of forming a catheter shaft having the layered construction described with reference to FIG. 1B to have uniform bending stiffness in a circumferential direction according to an embodiment hereof. In a step 570, a first component is extruded over a core mandrel. FIG. 6 is a cross-sectional view illustrating a first component 680 and a core mandrel 682. The first component 680 is formed entirely or solely of the first polymer described above having a first durometer and a first melting temperature. As described above, the first polymer is a relatively hard polymeric material that has the ability to withstand very high tensile and compressive forces during operation such as but not limited to polyetheretherketone (PEEK). Other suitable polymers for the first polymer are described in more detail herein. In an embodiment hereof, at body temperature, the first polymer has a tensile strength between 9,000 and 11,000 psi, a flexural strength between 19,000 and 21,000 psi, and a compressive strength between 14,000 and 16,000 psi. In another embodiment hereof, at body temperature, the first polymer has a tensile strength of 10,000 psi, a flexural strength of 20,000 psi, and a compressive strength of 15,000 psi.

The first component 680 includes an inner layer 650 and a plurality of first segments 656 of an outer layer 660. The plurality of first segments 656 radially extend from the inner layer 650. A gap or notch 684 extends between each pair of adjacent first segments 656. Each first segment 656 and each notch 684 extends in an axial direction along an entire length or substantially the entire length of the inner layer 650. The mandrel 682 is not required to be utilized in the remaining method steps after the first component 680 is extruded, and thus the mandrel 682 is not shown in FIGS. 7-9. However, in another embodiment, the mandrel 682 may be left in place during the method steps of FIGS. 7-9.

Figure 7:
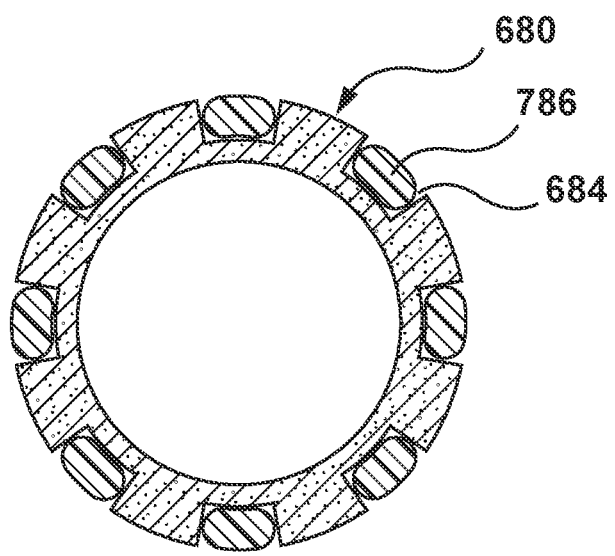
FIG. 7 is a cross-sectional view illustrating the first component and a plurality of segments of a second polymer described in the method of forming a catheter shaft of FIG. 5.

In a step 572, an elongated tube 786 of the second polymer described above having a second durometer and a second melting temperature is positioned into each notch 684 as shown in the cross-sectional view of FIG. 7. As described above, the second durometer of the second polymer is softer than the first durometer of the first polymer and the second melting temperature of the second polymer is lower than the first melting temperature of the first polymer. As described above, the second polymer has a second durometer softer than the first durometer of the first polymer. Further, the second polymer has a second melting temperature lower than the first melting temperature of the first polymer. The second polymer is a relatively soft polymeric material such as but not limited to thermoplastic polyurethane 80A that imparts flexibility to the catheter shaft and improves trackability of the delivery system 100. Other suitable polymers for the second polymer are described in more detail herein. In an embodiment hereof, at body temperature, the second polymer has a flexural strength between 4,000 and 6,000 psi. In another embodiment hereof, at body temperature, the second polymer has a flexural strength of 5,000 psi. Each elongated tube 786 extends in an axial direction along an entire length or substantially the entire length of the inner layer 650. Although shown with an oval cross-section which is sized to occupy the full thickness of the respective notch 684, each elongated tube 786 may have other cross-sections such as but not limited to circular or rectangular as the shape of each elongate tube 786 will change upon heating thereof.

Figure 8:
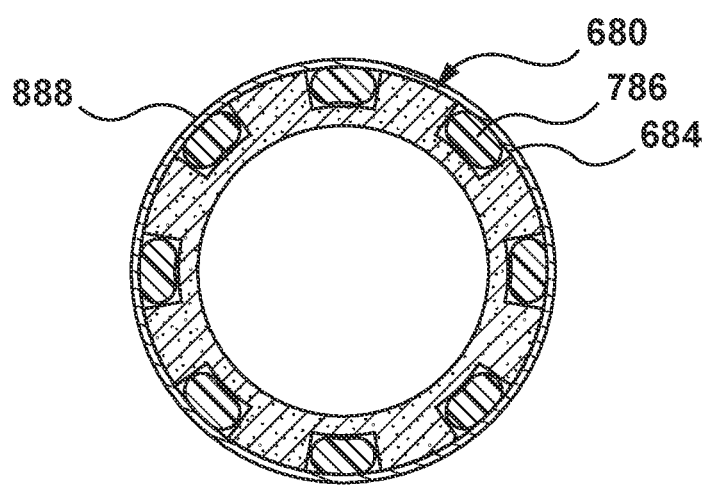
FIG. 8 is a cross-sectional view illustrating heat shrink tubing positioned over the first component and a plurality of segments of a second polymer described in the method of forming a catheter shaft of FIG. 5.

In a step 574, heat shrink tubing 888 is be positioned around the outer perimeter of the subassembly of the first component 680 and the plurality of elongated tubes 786. More particularly, as shown in FIG. 8, heat shrink tubing 888 is positioned over or around the first component 680 and the plurality of elongated tubes 786. Although FIG. 8 is a cross-sectional view, the heat shrink tubing 888 extends the full or entire length of the subassembly of the first component 680 and the plurality of elongated tubes 786.

Figure 9:
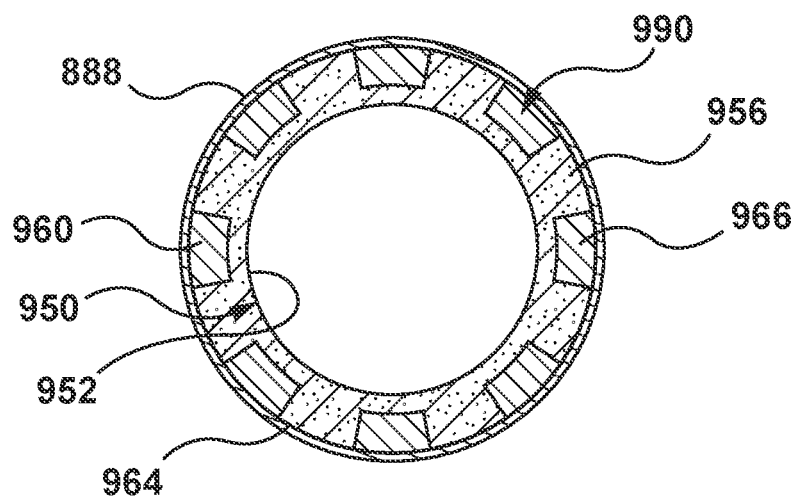
FIG. 9 is a cross-sectional view illustrating the heating step of the first component and a plurality of segments of a second polymer described in the method of forming a catheter shaft of FIG. 5.

In a step 576, with the heat shrink tubing 888 positioned thereover, the elongated tubes 786 of the second polymer are heated to fuse the elongated tubes 786 to the first component 680 and thereby form a catheter shaft 990 as shown in the cross-sectional view of FIG. 9. More particularly, heat is applied to the heat shrink tubing 888 in order to melt or reflow the plurality of elongated tubes 786 and thereby fuse the elongated tubes 786 to the first component 680.

Figure 10:
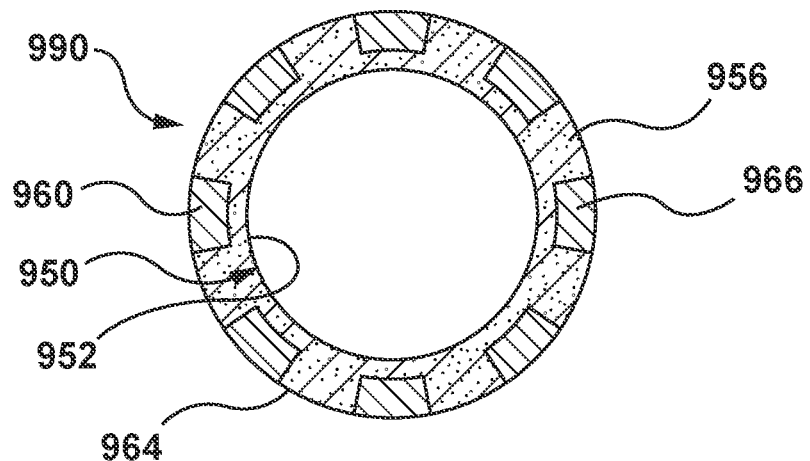
FIG. 10 is a cross-sectional view illustrating the catheter shaft formed via the method of forming a catheter shaft of FIG. 5 after the heating step and after removal from a mandrel.

The catheter shaft 990 is shown in FIG. 10 after the steps of heating the elongated tubes 786 and after removal of the heat shrink tubing 888. The catheter shaft 990 includes an inner layer 950 that defines, forms, or otherwise includes an innermost circumferential surface 952 of the catheter shaft 990 and an outer layer 960 that defines, forms, or otherwise includes an outermost circumferential surface 964 of the catheter shaft 990. The inner layer 950 is the same as the inner layer 150 described above with respect to the outer sheath 112, and the outer layer 960 is the same as the outer layer 160 described above with respect to the outer sheath 112. The inner layer 950 and the outer layer 960 directly contact each other with the outer layer 960 circumferentially surrounding the inner layer 950. The outer layer 960 is formed by alternating first and second segments 956, 966 of the first polymer and the second polymer, respectively, that alternate in a circumferential direction around the circumference of the outer layer 960. The first segments 956 alternate with the second segments 966, or stated another way, each first segment 956 is disposed between a pair of the second segments 966 and each second segment 966 is disposed between a pair of the first segments 956. Although only a cross-sectional view is shown in FIG. 10, each segment of the alternating first and second segments 956, 966 extends in an axial direction for an entire length or substantially the entire length of the catheter shaft 990. Stated another way, the cross-section of the catheter shaft 990 is the same as shown in FIG. 10 along an entire length or substantially the entire length of the catheter shaft 990. The first segments 956 are circumferentially spaced apart at equal intervals around the circumference of the outer layer 960, and the second segments 966 are circumferentially spaced apart at equal intervals around the circumference of the outer layer 960. In an embodiment, each segment of the alternating first and second segments 956, 966 are the same size or width. The outermost circumferential surface 964 of the catheter shaft 990 is smooth and continuous after the step of heating the elongated tubes 786 of the second polymer.

The catheter shaft 990 may be used, for example, as the outer sheath 112 and/or the middle shaft 122 of the delivery system 100 as described herein with respect to FIGS. 1-2, or alternatively may be a shaft used in any type of catheter device, including but not limited to balloon catheters, diagnostic catheters, drug delivery catheters, guide catheters, or any type of catheter device which it is desirable to have uniform bending stiffness in a circumferential direction combined with ability to withstand very high tensile and compressive forces during operation.

The foregoing description has been presented for purposes of illustration and enablement and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. A method of forming a catheter shaft comprising:
    extruding a first component of a first polymer having a first durometer and a first melting temperature, wherein the first component includes an inner layer defining an innermost circumferential surface and a plurality of segments radially extending from the inner layer and wherein a notch extends between each pair of adjacent segments of the plurality of segments, each segment of the plurality of segments extending in an axial direction for substantially an entire length of the inner layer;
    positioning an elongated tube of a second polymer having a second durometer and a second melting temperature into each notch, the second durometer being softer than the first durometer and the second melting temperature being lower than the first melting temperature; and
    heating the elongated tubes of the second polymer to fuse the elongated tubes of the second polymer to the first component and thereby form the catheter shaft, wherein the catheter shaft has a smooth and continuous outermost circumferential surface after the step of heating the elongated tubes of the second polymer.

2. The method of claim 1, wherein the first component is disposed over a core mandrel during extruding thereof.

3. The method of claim 2, wherein, at body temperature, the second polymer has a flexural strength between 4,000 and 6,000 psi.

4. The method of claim 3, wherein, at body temperature, the second polymer has a flexural strength of 5,000 psi.

5. The method of claim 3, wherein the second polymer is a thermoplastic polyurethane.

6. The method of claim 1, wherein heat shrink tubing is disposed around the first component and the elongated tubes during heating thereof.

7. The method of claim 6, wherein heat is applied to the heat shrink tubing in order to reflow the elongated tubes and thereby fuse the elongated tubes to the first component.

8. The method of claim 1, wherein the plurality of segments radially extending from the inner layer includes at least five segments.

9. The method of claim 1, wherein the plurality of segments radially extending from the inner layer includes between five and ten segments.

10. The method of claim 1, wherein each notch extending between a pair of adjacent segments of the plurality of segments is the same size.

11. The method of claim 10, wherein each segment of the plurality of segments is the same size as each notch.

12. The method of claim 1, wherein the second polymer is a thermoplastic polyurethane and the first polymer is PEEK.

13. The method of claim 1, wherein the catheter shaft has uniform bending stiffness in a circumferential direction.

14. The method of claim 1, wherein the catheter shaft is devoid of axial wires.

15. The method of claim 1, wherein the catheter shaft includes a first layer defining an innermost circumferential surface of the catheter shaft and defining a lumen of the catheter shaft, wherein the first layer is formed of the first polymer.

16. The method of claim 15, wherein the catheter shaft includes a second layer formed by alternating segments of the first polymer and the second polymer, respectively, that alternate in a circumferential direction, each segment of the alternating segments extending in an axial direction for substantially an entire length of the catheter shaft and the alternating segments collectively defining the outermost circumferential surface of the catheter shaft.

17. The method of claim 16, wherein the second layer of the catheter shaft has a radial thickness between the first layer and the outermost circumferential surface, and wherein each segment of the alternating segments extends the radial thickness of the second layer.

18. The method of claim 1, wherein, at body temperature, the first polymer has a tensile strength between 9,000 and 11,000 psi, a flexural strength between 19,000 and 21,000 psi, and a compressive strength between 14,000 and 16,000 psi.

19. The method of claim 18, wherein, at body temperature, the first polymer has a tensile strength of 10,000 psi, a flexural strength of 20,000 psi, and a compressive strength of 15,000 psi.

20. The method of claim 18, wherein the first polymer is polyetheretherketone (PEEK).

* * * * *